(12) United States Patent
Fedynyshyn et al.

(10) Patent No.: US 7,745,102 B2
(45) Date of Patent: Jun. 29, 2010

(54) IMMERSION FLUIDS FOR LITHOGRAPHY (75) Inventors: Theodore H. Fedynyshyn, Sudbury, MA (US); Indira Pottebaum, Boston, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 374 days.

(21) Appl. No.: 11/754,615

(22) Filed: May 29, 2007

(65) Prior Publication Data

US 2008/0063989 A1 Mar. 13, 2008

Related U.S. Application Data (60) Provisional application No. 60/809,060, filed on May 26, 2006, provisional application No. 60/831,790, filed on Jul. 19, 2006.

(51) Int. Cl.
*G03F 7/26* (2006.01)
(52) U.S. Cl. ..................................... 430/322
(58) Field of Classification Search ............... 430/322
See application file for complete search history.

(56) References Cited

U.S. PATENT DOCUMENTS

| 4,108,794 | A | 8/1978 | Yonekubo | |
|---|---|---|---|---|
| 4,677,049 | A * | 6/1987 | Griffing et al. | 430/339 |
| 2004/0009425 | A1 | 1/2004 | French et al. | |
| 2004/0137361 | A1* | 7/2004 | French et al. | 430/270.1 |
| 2004/0175647 | A1 | 9/2004 | French et al. | |
| 2005/0024609 | A1 | 2/2005 | De Smit et al. | |
| 2005/0029180 | A1 | 2/2005 | Kimisawa | |
| 2005/0122497 | A1* | 6/2005 | Lyons et al. | 355/53 |
| 2005/0145821 | A1 | 7/2005 | French et al. | |
| 2005/0161644 | A1 | 7/2005 | Zhang et al. | |
| 2005/0164522 | A1 | 7/2005 | Kunz et al. | |
| 2005/0186513 | A1* | 8/2005 | Letz et al. | 430/320 |
| 2005/0186514 | A1 | 8/2005 | French et al. | |
| 2007/0164261 | A1* | 7/2007 | Miyamatsu et al. | 252/582 |
| 2007/0296939 | A1* | 12/2007 | Nishii | 355/53 |
| 2009/0011375 | A1* | 1/2009 | Hirayama et al. | 430/325 |
| 2009/0081594 | A1* | 3/2009 | Chen et al. | 430/322 |

FOREIGN PATENT DOCUMENTS

| JP | 07-242675 | 9/1995 |
|---|---|---|
| JP | 07-247293 | 9/1995 |
| JP | 07-330782 | 12/1995 |
| JP | 2756410 | 5/1998 |
| WO | WO 2005/114711 | * 12/2005 |
| WO | WO 2005/117074 | 12/2005 |

OTHER PUBLICATIONS

Invitation to Pay Addtl Fees with Partial International Search, from corresponding PCT/US07/012648, mailed Mar. 14, 2008.
Irisawa et al., "The Modeling of Immersion Liquid by Using Quantum Chemical Calculation," Proc. SPIE 5754(1):1040-48 (2004).
Froberger, C.F., "Synthesis of Tetra(perfluoroalkoxy)silanes," J. Organic Chem. 25:311 (1960).

* cited by examiner

*Primary Examiner*—Cynthia H Kelly
*Assistant Examiner*—Anca Eoff
(74) *Attorney, Agent, or Firm*—Nutter McClennen & Fish LLP; Thomas J. Engellenner; Charlton Shen (57) ABSTRACT

Compositions for use as immersion fluids are described. In general, the immersion fluids can be utilized to perform lithography at short wavelengths (e.g., in a range from about 120 nm to about 260 nm). Some embodiments can be used in a range of actinic radiation between about 140 nm and about 160 nm (e.g., about 157 nm). Immersion fluids can exhibit any number of advantageous features including a relatively high index of refraction (e.g., greater than about 1, or greater than about 1.3, or about greater than about 1.4) and/or a relatively low absorbance (e.g., lower than about 2 $\mu m^{-1}$, or lower than about 1 $\mu m^{-1}$, or lower than about 0.5 $\mu m^{-1}$). Some immersion fluids can include silicon-containing compounds and/or germanium containing compounds. Such compounds can include at least one Ge—O bond or at least one Si—O bond. Such compounds can also include one or more fluorinated moieties.

26 Claims, 1 Drawing Sheet

FIG. 1

IMMERSION FLUIDS FOR LITHOGRAPHY

CROSS REFERENCE TO RELATED APPLICATIONS

The present application claims the benefit of a U.S. Provisional Patent Application entitled "Immersion Fluids for Lithography," bearing Ser. No. 60/809,060, filed on May 26, 2006; and also claims the benefit of a U.S. Provisional Patent Application entitled "Immersion Fluids for Lithography," bearing Ser. No. 60/831,790, filed on Jul. 19, 2006. Both applications are hereby incorporated herein by reference in their entirety.

STATEMENT OF GOVERNMENT SUPPORT

This invention was made with government support under Contract No. FA8721-05-C-0002 awarded by DARPA/MTO. The government has certain rights in the invention.

FIELD OF THE APPLICATION

The present application relates generally to compositions, compounds and methods for use in manufacturing materials such as electronics by photolithography, and more particularly to immersion fluids for use in photolithography at a variety of wavelengths such as about 157 nm.

BACKGROUND OF THE APPLICATION

Optical lithography at UV wavelengths is the standard process for patterning 90-nm state-of-the-art devices in the semiconductor industry, and extensions to 45-nm and below are currently being explored. Advanced lithographic schemes are focused on the use of a short UV wavelength (e.g., 193 nm or 157 nm), coupled with immersion to further reduce the effective wavelength.

Mass-produced semiconductor manufacturing entered the era of nanopatterning with UV optical lithography when the smallest feature sizes crossed the 100-nm threshold. In the last two years advanced devices have had their half-pitch at 90 nm and, according to the international roadmap for semiconductors (ITRS), this trend will continue unabated for at least one more decade with expected resolution decreasing to 65 nm in 2007, 45 nm in 2010, and 32 nm in 2013.

Until the late 1980s, the radiation sources were high-power mercury lamps, first at 436 nm, followed by 365 nm, and finally 254 nm. Then, a transition took place to the krypton fluoride excimer lasers at 248 nm, and more recently to the argon fluoride excimer lasers at 193 nm, and eventually to molecular fluorine lasers at 157 nm. Today, both 193- and 157-nm lithography is the subject of intense development, and significant progress is being made towards implementation at these wavelengths.

Several years ago a new technology was proposed, that of liquid immersion lithography, which, when implemented at 193 nm, would provide similar resolutions as "dry" 157 nm, without the risks involved in 157-nm lithography. Since early 2003, 193-nm liquid immersion lithography has taken center stage as the next generation of optical lithography. It now appears that "dry" 157-nm lithography will become a backup technology to 193-nm liquid immersion while liquid immersion 157-nm lithography is a likely candidate to be the successor to the liquid 193-nm lithography.

Submicrometer-scale optical imaging typically utilizes close proximity (<1 cm) between the focal plane and the final element of the imaging optics. Whereas normally this small space between the focal plane and the final optical element is filled with air, when it is filled with a fluid possessing a refractive index appreciably higher than 1.0, smaller features can be resolved and hence the imaging system exhibits improved resolution. This phenomenon has been well recognized for many years and this type of optical imaging is generally referred to as "immersion lithography" because it requires the focal plane to be immersed in the high-index fluid.

Liquid immersion lithography involves the introduction of a fluid between the last optical element and the photoresist surface. The effective wavelength of the imaging system is reduced in proportion to the index of refraction of the liquid. Since the performance of projection optics is essentially limited by diffraction, the shorter effective wavelength ($\lambda_{eff} = \lambda_o / n_f$ in a fluid of index $n_f$) enables a higher resolution when the vacuum wavelength $\lambda_o$ and $\theta$, the angle of propagation between the lens and the photoresist, remain constant. The second benefit of liquid immersion lithography is the increased depth of focus, even at dimensions that can be patterned in air. For a fixed feature size, $\theta$ in the fluid is smaller than in air, and consequently the aerial image is less sensitive to displacements of the photoresist surface along the optical axis. This reduced sensitivity is equivalent to a larger depth of focus. Thus, liquid immersion lithography allows for higher resolution or increased depth of focus relative to dry lithography.

In dry lithography, the largest NA possible is 1.0, which is defined in part by the refractive index of air being 1.0. In liquid immersion lithography, a fluid is introduced between the last optical element and the photoresist and in so doing, the NA of the projection optics is effectively increased to above 1.0. For example, the 193-nm refractive index of high-purity water is ~1.44, and this is therefore the upper limit of the NA using water at 193 nm. Viewed another way, the vacuum wavelength of 193 nm is reduced by the refractive index of water to an effective wavelength of 134 nm in the image plane. This value is less than 157 nm, implying that a higher resolution is possible with 193 nm and water immersion than with dry 157 nm. A similar reduction in effective wavelength would be possible employing liquid immersion at 157 nm.

Manufacturing of integrated circuits has been enabled by high-performance spin-on organic polymeric photoresists. The development of polyhydroxystyrene based resists was necessary to overcome high novolac absorbance at 248 nm and enable the introduction of 248 nm lithography into IC manufacturing. In a similar manner, 193-nm lithography required the development of a new polymer system to overcome the high 193-nm absorbance of phenolic-based polymers. Two different classes of polymers, polyacrylate and polycyclic copolymer based resists have been developed, and now compete for predominance in 193-nm lithography. Due to the high absorbance at 157 nm of polyhydroxystyrene, polyacrylate, and polycyclic copolymer based resists, the use of any of these resists will only be possible if the coated resist thickness is under 100 nm. This has led to the development of fluorinated polymers as resist materials capable of high resolution. Liquid immersion lithography can utilize some of the same types of photoresists as employed in dry lithography although there are concerns about leaching of chemicals from the photoresists and the effect of that leaching on resist resolution and optical lens contamination.

One difficulty associated with developing high refractive index fluids for immersion lithography relates to solving the requirement for a fluid to have both high index and low absorbance. For example, the addition of fluorine to a liquid's molecular formula will reduce not only the molecule's absorbance but also its refractive index. Current liquids employed for 157-nm immersion lithography are fluorocarbon or fluorohydrocarbon based and have refractive indices at 157-nm of less than 1.35.

Hence, there is still a need for improved immersion liquids suitable for use in immersion lithography at very short wavelengths, e.g., at 157 nm. There is also a need for such liquids that exhibit not only a high refractive index but also a relatively low absorbance.

SUMMARY

Aspects of the present invention are directed to compositions for use as immersion fluids. In general, the immersion fluids can be utilized to perform lithography at short wavelengths (e.g., in a range from about 120 nm to about 260 nm) by acting to decrease the effective wavelength of the actual wavelength emitted by a radiation source. Some immersion fluids can be particularly useful with a range of actinic radiation between about 140 nm and about 160 nm (e.g., about 157 nm). Immersion fluids can exhibit any number of advantageous features including a relatively high index of refraction (e.g., greater than about 1, or greater than about 1.3, or about greater than about 1.4) and/or a relatively low absorbance (e.g., lower than about 2 $\mu m^{-1}$, or lower than about 1 $\mu m^{-1}$, or lower than about 0.5 $\mu m^{-1}$). Immersion fluids can include silicon-containing compounds and/or germanium containing compounds. Such compounds can include at least one Ge—O bond or at least one Si—O bond. Such compounds can also include one or more fluorinated moieties.

Some aspects are generally directed to immersion liquids having sufficiently high indices of refraction that would render them suitable for use in short wavelength photolithography, e.g., at 157 nm. Further, embodiments of the invention relate generally to processes for performing photolithography, as well as associated lithographical systems, that make use of such fluids. By way of example, the use of liquid immersion lithography with the proper immersion liquids of sufficiently high index can allow for half-pitch printing at 193 nm to extend to the 32-nm lithography node of the ITRS Roadmap and for half-pitch printing at 157 nm to extend to the 22-nm lithography node of the ITRS Roadmap.

One aspect of the invention is directed to a process for performing photolithography with actinic radiation having at least one wavelength below about 260 nm. The radiation can have a wavelength in a range of about 140 nm to about 260 nm; or in a range of about 140 nm to about 200 nm; or in a range of about 140 nm to about 160 nm. A liquid can be disposed such that the radiation passes through at least a portion of the liquid before impinging on a surface. The liquid can include a silicon-containing compound, a germanium-containing compound, or both. For example, the compound can include at least one of a Si—O bond and a Ge—O bond. Alternatively, or in addition, the compound can include at least one fluorinated moiety. The liquid can be deoxygenated. In one embodiment, the liquid can have a molecular oxygen concentration below about 1000 ppm. The liquid can also exhibit an index of refraction greater than about 1, or about 1.3, or about 1.35, or about 1.4.

Another aspect of the invention is directed to a composition for use as an immersion fluid in photolithography. The immersion fluid can be a liquid exhibiting an index of refraction greater than about 1.3, or greater than about 1.4. The fluid can also exhibit an absorbance less than about 2 $\mu m^{-1}$ or less than about 1 $\mu m^{-1}$ for light having at least one wavelength in a range from about 140 nm to about 160 nm. The immersion fluid can include a compound having at least one fluorinated moiety. The immersion fluid can be a liquid which exhibits a decomposition of less than about 1 weight percent after about 1 hour of exposure to air, and/or be a liquid that is deoxygenated.

Other aspects of the invention are directed to a composition that includes a compound having at least one Si—O bond. The silicon atom of the Si—O bond can be attached to at least one additional oxygen. As well, the Si—O bond can form a cyclic structure with one or more additional Si—O bonds present in the compound. Examples of compounds include organosilanes, trisiloxanes, tetrasiloxanes, and caged siloxanes (e.g., a polyhedral silsesquioxane). The compound can also include fluorine and/or a fluorinated moiety optionally attached to an oxygen atom of the Si—O bond. Potential fluorinated moieties include any of a fluorinated alkyl, a fluorinated alkoxy, a fluorinated alkenyl, a fluorinated aryl, a fluorinated heteroaryl, a fluorinated silanyl, a fluorinated siloxynyl, or a fluorinated heteroalkyl. In one embodiment, the composition comprises a compound that includes at least one Si—O bond, with a cyclic structure formed with one or more additional Si—O bonds, at least one oxygen atom of the Si—O bond being attached to a fluorinated moiety. Such a liquid can have an index of refraction greater than 1 for at least one wavelength in a rage of about 140 nm to about 260 nm. In another embodiment, when the compound has only 1 silicon atom and the Si atom is attached to an aliphatic moiety, the fluorinated moiety is either a linear fluorinated moiety, or a branched fluorinated moiety with at least 4 carbon atoms. In yet another embodiment, when the compound has only 1 silicon atom and the Si atom is attached to 4 oxygen atoms, the fluorinated moiety has at least 4 carbon atoms.

Another aspect of the invention is directed to a composition that includes a compound having at least one Ge—O bond. The germanium atom of the Ge—O bond can be attached to at least one additional oxygen. The oxygen atom of the Ge—O bond can be attached to a fluorinated moiety. Potential fluorinated moieties include any of a fluorinated alkyl, a fluorinated alkoxy, a fluorinated alkenyl, a fluorinated aryl, a fluorinated heteroaryl, a fluorinated germanyl, a fluorinated germanoxanyl or a fluorinated heteroalkyl. The Ge—O bond can also form a cyclic structure with one or more additional Ge—O bonds present in the compound. Examples include organogermoxanes, trigermoxanes, tetragermoxanes, and caged germoxanes. In one embodiment, the composition comprises a liquid having a compound including at least one Ge—O bond, the oxygen atom of the Ge—O bond being attached to a fluorinated moiety. Such a liquid can have an index of refraction greater than 1 for at least one wavelength in a range of about 140 nm to about 260 nm.

Compositions for use as an immersion fluid can also include a variety of other features. The composition can be deoxygenated. In one embodiment, the composition can have a molecular oxygen concentration below about 1000 ppm. The composition, or parts of the composition, can exhibit a decomposition of less than about 0.5 weight %, or less than about 1 weight %, or less than about 2 weight % after about 1 hour of exposure in air. Alternatively, or in addition, the composition, or parts of the composition, can exhibit a decomposition of less than about 10 weight % after about 24 hours of exposure to air. The composition can have an index of refraction greater than 1, or greater than about 1.3, or greater than about 1.35, or greater than about 1.4, or greater than about 1.44. The composition can also, or alternatively, have an absorbance less than about 2 $\mu m^{-1}$, or less than about 1 $\mu m^{-1}$, or less than about 0.5 $\mu m^{-1}$. The absorbance and/or index of refraction can be relative to particular wavelength or wavelength range. For example, the wavelength can be less than 260 nm, or in a range of about 140 nm to about 260 nm, or in a range of about 140 nm to about 200 nm, or in a range of about 140 nm to about 160 nm. As well, the composition can exhibit liquid properties over a temperature range of about 10° C. to about 35° C. and/or a pressure range of about 250 torr to about 850 torr. The composition can also, or alternatively, exhibit a viscosity in a range of about 0 centipoise to about 300 centipoise.

DETAILED DESCRIPTION

Some embodiments of the present invention are generally drawn to immersion fluids suitable for use in performing photolithography, and the use of such fluids. In particular embodiments, the immersion fluids can be used at short wavelengths, e.g., in a range of about 120 nm to about 260 nm. It is surprisingly found that some embodiments pertaining to fluids with germanium-containing and/or silicon-containing compound(s) can result in liquids having relatively high index of refraction (e.g., greater than 1, or about 1.3, or about 1.35, or about 1.4), while having a relatively low absorbance (e.g., less than about 2 $\mu m^{-1}$, or less than about 1 $\mu m^{-1}$, or less than about 0.5 $\mu m^{-1}$) in particular short wavelength ranges (e.g., about 140 nm to about 260 nm, about 140 nm to about 200 nm, or about 140 nm to about 160 nm). Accordingly, these embodiments may be advantageous in extending the resolution of current lithographic techniques.

Liquid immersion lithography involves the introduction of a fluid between the last optical element of a lithographic system and a photoresist surface. The effective wavelength of the imaging system can be reduced in proportion to the index of refraction of the liquid. The use of liquid immersion lithography with the proper immersion liquids of sufficiently high index can allow for half-pitch printing at 193 nm to extend to the 32-nm lithography node of the ITRS Roadmap and for half-pitch printing at 157 nm to extend to the 22-nm lithography node of the ITRS Roadmap.

Figure 1:
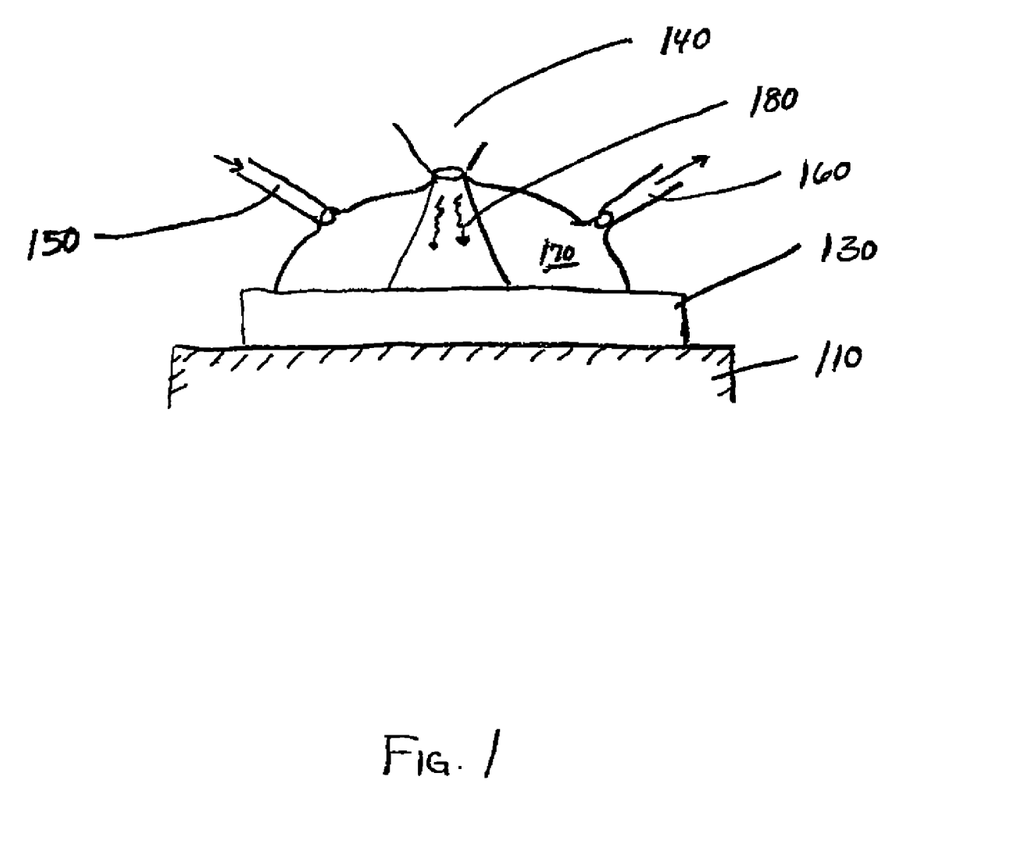
FIG. 1 is a schematic diagram of a liquid immersion lithography apparatus, in accord with some embodiments of the present invention.

Some embodiments drawn to the use of immersion fluids can be described with respect to the apparatus depicted in FIG. 1. A substrate 110 has a photoresist 130 formed thereon. Formation of the photoresist can be performed in accordance techniques known to those skilled in the art (e.g., spin casting), among others. A liquid layer 170 can contact a portion of the photoresist surface 130 (e.g., about 5 $cm^2$ to about 10 $cm^2$) and the final optical element of a radiation source 140. Radiation sources can constitute any source capable of emitting a desired wavelength or wavelength range (e.g., about 157 nm). The liquid 170 can be distributed through a outlet port 150 of a source and sucked into an inlet port 160 of a sink as depicted in FIG. 1. The liquid can be continuously circulated using the outlet 150 and inlet 160 ports, though other ways of forming and maintaining the liquid layer can also be utilized. An image pattern can be projected through the liquid layer 170, and onto the surface of the photoresist 130 using actinic radiation 180 with a short wavelength (e.g., less than about 260 nm). Subsequently, the liquid 170 can be completely removed, with selected portions of the photoresist also being removed using techniques discussed herein and known to those skilled in the art. Immersion fluids that can be utilized with such a process include any of the fluids/compositions/compounds described herein (e.g., germanium-containing compounds and silicon-containing compounds). As well, the immersion fluids can be relatively free of contaminants such as molecular oxygen and water.

Though the immersion fluids discussed herein can be utilized at a variety of actinic radiation wavelengths, in some embodiments the fluids are effective for short wavelength lithography (e.g., less than about 260 nm). For example, the immersion fluid can be utilized with an actinic radiation in a range of about 140 nm to about 260 nm, or about 140 nm to about 200 nm, or about 140 nm to about 160 nm. Immersion fluids that can be utilized in such ranges are potentially useful for performing lithography at wavelengths of about 248 nm, about 193 nm, and about 157 mm.

In some embodiments, an immersion fluid can possess a relatively high refractive index at a desired imaging wavelength (e.g., any of the wavelength(s) or ranges of wavelengths described herein). Any refractive index greater than that of air (i.e., 1.0) can produce a desirable result since the effective wavelength is typically $\lambda_{eff}=\lambda_o/n_f$ in a fluid of index $n_f$. In some embodiments, the refractive index can be greater than about 1.3, or greater than about 1.35, or greater than about 1.4. In one embodiment, the index of refraction can be greater than about 1.44 for light with a wavelength of about 193 nm.

Immersion fluids can alternatively, or in addition, possess a relatively low absorbance at a desired imaging wavelength. The absorbance can vary with the optical path length such that the optical density of the fluid is typically less about 2 $\mu m^{-1}$, less than about 1 $\mu m^{-1}$, or preferably less about 0.5 $\mu m^{-1}$. For example, for a 2 micrometer path length the absorbance can be no greater than 0.25 $\mu m^{-1}$.

In some embodiments, the presence of a contaminant in an immersion fluid can detrimentally impact the absorption characteristics of the fluid for a given wavelength. For example, molecular oxygen and water each absorb radiation substantially at a wavelength of about 157 nm. Accordingly, the presence of either specie in an excessive amount can increase the absorbance of the fluid above a desirable range. Thus, in some embodiments, an immersion fluid can have less than about 100 ppm of water present, or less than about 1000 ppm of water present, or less than about 10000 ppm of water present. In other embodiments, an immersion fluid can have less than about 100 ppm of molecular oxygen present, or less than about 1000 ppm of molecular oxygen present, or less than about 10000 ppm of molecular oxygen present. In still other embodiments, the amount of molecular oxygen and water present in an immersion fluid can comprise any combination of the potential limits discussed above. The ppm values stated herein are on a weight basis unless otherwise explicitly stated.

As utilized throughout the present application, the term "deoxygenated" is defined as having a molecular oxygen concentration below about 10000 ppm by weight. That is to say apart from the oxygen atoms bonded to silicon and/or germanium, in some exemplary immersion fluids, the presence of free oxygen, e.g., as $O_2$, in the composition is insignificant.

It is understood that other compounds that adversely affect an immersion fluid (e.g., the absorption and/or index of refraction) can also be held at or below a selected level, consistent with embodiments of the present invention. By way of example, certain compounds that absorb particular wavelengths of light can be deemed "impurities" with respect to a composition for which having minimal absorbance below that wavelength was desirable. Examples of such compounds can include those having at least one alkene, e.g., a compound that includes a vinyl group, an aromatic or heteroaromatic ring, or a diene. Impurities can also include those from compounds having at least one carbonyl group, for example, a ketone, an aldehyde, carboxylic acid, ester, anhydride, or an acid fluoride. Chlorinated compounds, or metals or metallic salts can be an impurity in an immersion fluid composition. In some embodiments, unsaturated compounds, including unsaturated compounds with low boiling points, can be such impurities. It is understood that for all of those instances in which the foregoing compounds are understood to be impurities with respect to a subject composition, such composition may contain some of them, but not so much that such composition no longer has the desired characteristics. It is also understood that particular compounds that have some structural similarity to one or more of the named "impurities" above may not be impurities if the particular compound exhibits a desired property of an immersion fluid (e.g., compound exhibits a relatively low absorbance).

Because properties such as index of refraction and absorbance at one or more wavelengths can be important in some immersion fluids, some embodiments are drawn to immersion fluids that exhibit a selected purity level. In certain embodiments, an immersion fluid can be purified (or otherwise prepared) to achieve a desired absorbance or index of refraction. In some embodiments, the fluid composition of the present invention has at least about 99.9% purity by weight, at least 99.99% purity by weight, at least 99.999% purity by weight, or even at least 99.9999% purity by weight of one or more compounds in the composition. The non-pure fraction of the composition can comprise water, molecular oxygen, any of the impurities previously described, or other contaminants. These contaminants in the fluid composition may contribute to a higher absorbance of the fluid at wavelengths less than about 260 nm, less than about 200 nm, or less than about 160 nm. Techniques for purifying an immersion fluid can include any of those known to the skilled artisan (e.g., bubbling nitrogen gas through the fluid for a sufficiently long period of time).

In some embodiments, it can be advantageous for the immersion fluid to possess a relatively high refractive index and a relatively low absorbance. Such combination can utilize any of the values or ranges for absorbance or refractive index discussed herein. For example, the composition of an immersion fluid may have an index of refraction greater than about 1 and an absorbance of less than about 2 $\mu m^{-1}$; or an index of refraction greater than about 1.35 and an absorbance of less than about 2 $\mu m^{-1}$ or less than about 1 $\mu m^{-1}$; or an index of refraction greater than about 1.4 and an absorbance less than about 1 $\mu m^{-1}$. Other combinations are also within the scope of the present disclosure. These combinations can also be associated with a particular wavelength or wavelength range, such from about 140 nm to about 260 nm; from about 140 nm to about 200 nm; and from about 140 nm to about 160 nm. Such fluids can also include one or more other characteristics as described herein (e.g., having a molecular oxygen concentration below about 10000 ppm, and/or including a compound having a fluorinated moiety as described herein).

In general, immersion fluids can exhibit liquid-like characteristics over an operating range typical for performing liquid immersion lithography. For instance, a composition suitable for use in liquid immersion lithography can exhibit a liquid state over a nominal environmental temperature range (e.g., between about 10° C. and about 35° C.) and/or a nominal atmospheric pressure range (e.g., about 250 torr to about 850 torr). In another instance, a composition suitable for liquid immersion lithography can exhibit a vapor pressure between about 0.001 torr and about 500 torr. In still another instance, a suitable composition exhibits a viscosity between about 1 centipoise and about 300 centipoise. Immersion fluids consistent with embodiments of the present invention can utilize any number of these characteristics.

As well, it can be desirable for a liquid immersion composition to exhibit a particular range of stability in air, i.e., such that a compound only decomposes to a particular extent over a given period of time. As used herein "air" refers to typical sea-level atmosphere, which can be further defined to be at a pressure of 1 bar and a temperature of 25° C. For example, an immersion fluid consistent with an embodiment of the invention can include the compound trihexafluoroisopropoxy methysilane. This silane, however, exhibits relatively rapid decomposition in air, losing 10% or more of its weight in about a 10 minute period. Another silane, tetra(1H,1H-heptafluoro-1-butoxy)silane, exhibits a decomposition in air of about 15 weight % over a period of about 24 hours. So while both of these silanes can be used in an immersion fluid in some environments, utility of these compounds in typical atmospheric conditions can be constrained.

Accordingly, some particular embodiments can be drawn to a composition of an immersion fluid that exhibits a decomposition of less than a selected weight percent over a selected period of time in air. It is understood that decomposition of 1% by weight over a 1 hour period is equivalent to saying that 99% by weight of the original form of the material is still present after a 1 hour time period. Examples of decomposition can be less than about 0.1%, 0.5%, 1%, 2%, 5%, 10%, 15%, or 20% by weight over a time period of about 1 hour, 12 hours, or 24 hours when exposed to air. In one example, the decomposition can be less than about 1 weight percent after about 1 hour of exposure to air. In another example, the decomposition can be less than about 10 weight percent after about 24 hours of exposure to air. It is understood that these decomposition values are cumulative values after a pure composition is first exposed to air, and do not necessarily imply a linear decomposition rate over the time period selected.

Immersion fluids consistent with embodiments of the invention can utilize one or more components such that the fluid has desirable characteristics (e.g., relatively low absorbance and relatively high index of refraction). Though immersion fluids can utilize any number of components, some embodiments of the present invention are drawn to compositions that include a liquid having at least one germanium-containing specie and/or at least one silicon containing specie (e.g., an organosilane or a siloxane). For example, the fluids can include one or more of the germanium-containing or silicon-containing species at a selected purity level, e.g., having sufficient purity such that the fluid has a particular absorbance level. In another example, an immersion fluid comprises a compound that includes at least one of a germanium-containing compound and a silicon-containing compound, and other immersion fluid components (e.g., compositions known to those skilled in the art). Such combinations of compounds can be formulated to provide an immersion fluid with any combination of the properties described within the present application (e.g., a relatively high index of refraction and/or a relatively low absorbance).

In some cases, the fluids have the special feature of including a compound having at least one oxygen atom directly bonded to the silicon or germanium to yield a silicon-oxygen or germanium-oxygen bond. In some embodiments, the compound can have up to four oxygen atoms bonded to the silicon or germanium and, in some preferred embodiments, each silicon or germanium can be either two or three oxygen atoms bonded thereto. Examples of some of the simplest structures are shown below where the germanium atom is bonded to either one, two, three, or four oxygen atoms (e.g., bi, tri, and tetragermoxanes) and where the silicon atom is bonded to either one, two, three, or four oxygen atoms (e.g., bi, tri, and tetrasiloxanes). Other structures are also contemplated such as organosiloxanes and organogermoxanes.

Exemplary Structures (1)

Silicon Bonded to Either One, Two, Three, or Four Oxygen Atoms

Exemplary Structures (2)

Germanium Bonded to Either One, Two, Three, or Four Oxygen Atoms

Compounds useful for immersion fluids are not limited to those containing only one silicon or germanium atom. In some cases, it can be advantageous for the immersion fluid to contain multiple silicon or germanium atoms connected by an oxygen atom to form silicon-oxygen or silicon-germanium chains. Examples of these types of compounds are shown below, where the silicon or germanium fluid can be a dimer where n is equal to 0, an oligomer where n is between 1 and 10, or a polymer where n is greater than 10. Although these structures are shown below as linear, in some fluids with multiple silicon or germanium atoms, the chain can be linear or branched and both types can be used in an immersion fluid.

Exemplary Structures (3)

Compounds Containing Multiple Silicon and Germanium Atoms

In some embodiments, the compound(s) used in an immersion fluid can be cyclic in that the silicon-oxygen or silicon-germanium chain is not terminated but instead forms a cyclic structure as shown below. The value of n can be any number equal to or greater than zero, but is preferably between one and ten and most preferably to be between one and three.

Exemplary Structures (4)

Cyclic Immersion Fluids Containing Multiple Silicon and Germanium Atoms

Cyclic immersion fluids can also include compounds exhibiting more complexity and/or three-dimensional structure. Accordingly, some compounds that can be used in an immersion fluid include "caged" siloxanes, "caged" germoxanes, and derivatives thereof. One example of such compounds are polyhedral silsesquioxanes, which can exhibit a three-dimensional cage of silicon and oxygen bonds. These compounds can be substituted with any number of substitutents, e.g., the R groups described herein when chemically appropriate. In some embodiments, the substitutions are aliphatic groups. In some embodiments, these compounds are substituted with one or more fluorinated moieties as described in further detail herein.

Compounds containing more than one silicon or germanium atoms need not contain only Si—O—Si or Ge—O—Ge bonds as shown above. In some embodiments, the immersion fluids containing more that one silicon or germanium atom can have any number of intervening atoms between the silicon or germanium atoms. These intervening atoms can be oxygen, but the fluid will also be effective if the linking atoms do not contain oxygen. In some embodiments, each silicon or germanium atom is attached to an oxygen atom. Examples of compounds containing more than one silicon or germanium atom but not having a Si—O—Si or Ge—O—Ge bond are shown below. Immersion fluids of this type can be linear, branched, or cyclic (e.g., polycyclic).

Exemplary Structures (5)

Immersion Fluids Containing Multiple Silicon and Germanium Atoms

As noted above, in many embodiments, an immersion fluid includes a compound in which each silicon or germanium atom is attached to an oxygen atom. Other chemical elements and functional groups can also be present in the compound and these chemical elements and functional groups will act to improve the immersion fluid properties. By way of example, the R groups shown in the above Exemplary Structures (1) to (5) can be substituted or unsubstituted alkyl, alkenyl, alkoxy, alkynyl, aryl or heteroaryl, silanyl, siloxanyl, germanyl, germanoxanyl, or heteroalkyl.

In some embodiments of the invention, some or all of the R groups are substituted with fluorine or a fluorine moiety. Fluorine substitution of a compound used in an immersion fluid can lower the overall absorbance of the fluids in the range of about 120 to 260 nm. Fluorine substitution may also lower the refractive index of fluids in the range of about 120 to 260 nm. It is therefore desirable that some of the hydrogen atoms bound to carbon on the R groups are replaced with fluorine. For instance, this will yield R groups that are either hydrocarbons, fluorohydrocarbons, fluorocarbons, or any mixture thereof. In one example, a compound for use in an immersion fluid includes at least one Ge—O bond, where an oxygen atom connected to a germanium atom is also attached to a fluorinated moiety. The germanium atom of the Ge—O can optionally be attached to another oxygen atom.

Fluorinated moieties include the variety of substitutions described herein, including moieties where at least one hydrogen substituent is replaced by a fluorine atom. Examples of fluorinated moieties include any of a fluorinated alkyl, a fluorinated alkoxy, a fluorinated alkenyl, a fluorinated aryl, a fluorinated heteroaryl, a fluorinated germanyl, a fluorinated germanoxanyl or a fluorinated heteroalkyl. Some examples of a Ge—O compound include Materials 13, 14, and 22 described in the Examples section below. Another example can include a cyclic structure containing a germanium-oxygen backbone (e.g., the cyclic structure with germanium shown in Exemplary Structures 4) with at least one fluorinated moiety attached to an oxygen in the cyclic backbone. As well, such Ge—O compounds can be used to make an immersion fluid with particular properties relative to actinic radiation (e.g., having an index of refraction greater than about 1.3 for radiation wavelengths in a range from about 140 nm to about 260 nm; and/or having an absorbance less than about 1 $\mu m^{-1}$ for radiation wavelengths in a range from about 140 nm to about 260 nm).

Though some embodiments utilizing silicon-containing compounds can be fluorinated in one or more positions, wherever potentially possible in the compound, in another example a compound for use in an immersion fluid includes at least one Si—O bond, where an oxygen atom connected to a silicon atom is also attached to a fluorinated moiety (e.g., a fluorinated organosilane). Fluorinated moieties include the variety of substitutions described herein, including moieties where at least one hydrogen substituent is replaced by a fluorine atom. Fluorinated moieties can comprise any of a fluorinated alkyl, a fluorinated alkoxy, a fluorinated alkenyl, a fluorinated aryl, a fluorinated heteroaryl, a fluorinated silanyl, a fluorinated siloxynyl, or a fluorinated heteroalkyl. Some examples of such a compound are molecules having one silicon atom, where the silicon is attached to a substituted or unsubstituted aliphatic moiety, and the oxygen atom is attached to a linear fluorinated moiety, or a branched fluorinated moiety with 4 or more carbon atoms. Another example includes molecules where a silicon atom is attached to 4 oxygen atoms, each oxygen atom being attached to a fluorinated moiety. Each of the fluorinated moieties can include 4 or more carbon atoms. Another example can include a cyclic structure containing a silicon-oxygen backbone (e.g., the cyclic structure with silicon shown in Exemplary Structures 4) with at least one fluorinated moiety attached to an oxygen in the cyclic backbone. As well, such Si—O compounds can be used to make an immersion fluid with particular properties relative to actinic radiation (e.g., having an index of refraction greater than about 1.3 for radiation wavelengths in a range from about 140 nm to about 260 nm; and/or having an absorbance less than about 1 $\mu m^{-1}$ for radiation wavelengths in a range from about 140 nm to about 260 nm).

In some embodiments of the invention, some or all of the R groups have heteroatoms in the main chain. Some examples of suitable heteroatoms are nitrogen, oxygen, sulfur, phosphorus, or selenium, although any other heteroatoms can also be used. One particularly preferred embodiment is where the R groups are fluoroethers or fluorohydroethers.

Moreover, in some preferred embodiments of this invention, some or all of the R groups are substituted with heteroatoms. These heteroatoms can be added by a variety of chemical functional groups such as F, Cl, Br, I, OH, OR, $NR_2$, $NR_3$, $SiR_3$, $OSiR3$, $GeR_3$, $OGeR_3$, NCO, CN, O(CO)R, N(CO)R, $PR_2$, PR(OR), $P(OR)_2$, SR, SSR, $SO_2R$, $SO_3R$, SeR, SeSeR, $SeO_2R$, $SeO_3R$.

Herein, the term "aliphatic group" refers to a straight-chain, branched-chain, or cyclic aliphatic hydrocarbon group and includes saturated and unsaturated aliphatic groups, such as an alkyl group, an alkenyl group, and an alkynyl group.

The terms "alkenyl" and "alkynyl" refer to unsaturated aliphatic groups analogous in length and possible substitution to the alkyls described above, but that contain at least one double or triple bond respectively.

The terms "alkoxyl" or "alkoxy" as used herein refer to an alkyl group, as defined below, having an oxygen radical attached thereto. Representative alkoxyl groups include methoxy, ethoxy, propyloxy, tert-butoxy and the like. An "ether" is two hydrocarbons covalently linked by an oxygen.

The term "alkyl" refers to the radical of saturated aliphatic groups, including straight-chain alkyl groups, branched-chain alkyl groups, cycloalkyl(alicyclic) groups, alkyl-substituted cycloalkyl groups, and cycloalkyl-substituted alkyl groups. In preferred embodiments, a straight chain or branched chain alkyl has 30 or fewer carbon atoms in its backbone (e.g., $C_1$-$C_{30}$ for straight chains, $C_3$-$C_{30}$ for branched chains), and more preferably 20 or fewer. Likewise, preferred cycloalkyls have from 3-10 carbon atoms in their ring structure, and more preferably have 5, 6 or 7 carbons in the ring structure.

Moreover, the term "alkyl" (or "lower alkyl") as used throughout the specification, examples, and claims is intended to include both "unsubstituted alkyls" and "substituted alkyls", the latter of which refers to alkyl moieties having substituents replacing a hydrogen on one or more carbons of the hydrocarbon backbone. Such substituents can include, for example, a halogen, a hydroxyl, a carbonyl (such as a carboxyl, an alkoxycarbonyl, a formyl, or an acyl), a thiocarbonyl (such as a thio ester, a thio acetate, or a thioformate), an alkoxyl, a phosphoryl, a phosphate, a phosphonate, a phosphinate, an amino, an amido, an amidine, an imine, a cyano, a nitro, an azido, a sulfhydryl, an alkylthio, a sulfate, a sulfonate, a sulfamoyl, a sulfonamido, a sulfonyl, a heterocyclyl, an aralkyl, or an aromatic or heteroaromatic moiety. It will be understood by those skilled in the art that the moieties substituted on the hydrocarbon chain can themselves be substituted, if appropriate. For instance, the substituents of a substituted alkyl may include substituted and unsubstituted forms of amino, azido, imino, amido, phosphoryl (including phosphonate and phosphinate), sulfonyl (including sulfate, sulfonamido, sulfamoyl and sulfonate), and silyl groups, as well as ethers, alkylthios, carbonyls (including ketones, aldehydes, carboxylates, and esters), —$CF_3$, —CN and the like. Exemplary substituted alkyls are described below. Cycloalkyls can be further substituted with alkyls, alkenyls, alkoxys, alkylthios, aminoalkyls, carbonyl-substituted alkyls, —CF$_3$, —CN, and the like.

Unless the number of carbons is otherwise specified, "lower alkyl" as used herein means an alkyl group, as defined above, but having from one to ten carbons, more preferably from one to six carbon atoms in its backbone structure. Likewise, "lower alkenyl" and "lower alkynyl" have similar chain lengths. Throughout the application, preferred alkyl groups are lower alkyls, although other alkyls can also be employed. In preferred embodiments, a substituent designated herein as alkyl is a lower alkyl.

The term "heteroalkyl" as used throughout the specification, examples, and claims is intended to include both "unsubstituted alkyls" and "substituted alkyls," (the latter of which refers to alkyl moieties having substituents replacing a hydrogen on one or more carbons of the hydrocarbon backbone) in which one or more carbons of the hydrocarbon backbone is replaced by an atom of any element other than carbon or hydrogen. Preferred heteroatoms are boron, nitrogen, oxygen, phosphorus, sulfur, and selenium.

The term "alkylthio" refers to an alkyl group, as defined above, having a sulfur radical attached thereto. Representative alkylthio groups include methylthio, ethylthio, and the like.

The terms "amine" and "amino" are art-recognized and refer to both unsubstituted and substituted amines, e.g., a moiety that can be represented by the general formula:

wherein $R_9$, $R_{10}$ and $R'_{10}$ each independently represent a hydrogen, an alkyl, an alkenyl, —(CH$_2$)$_m$—R$_8$, or R$_9$ and R$_{10}$ taken together with the N atom to which they are attached complete a heterocycle having from 4 to 8 atoms in the ring structure; $R_8$ represents an aryl, a cycloalkyl, a cycloalkenyl, a heterocycle or a polycycle; and m is zero or an integer in the range of 1 to 8. In preferred embodiments, only one of $R_9$ or $R_{10}$ can be a carbonyl, e.g., $R_9$, $R_{10}$ and the nitrogen together do not form an imide. In even more preferred embodiments, $R_9$ and $R_{10}$ (and optionally $R'_{10}$) each independently represent a hydrogen, an alkyl, an alkenyl, or —(CH$_2$)$_m$—R$_8$. Thus, the term "alkylamine" as used herein means an amine group, as defined above, having a substituted or unsubstituted alkyl attached thereto, i.e., at least one of $R_9$ and $R_{10}$ is an alkyl group.

The term "amido" is art-recognized as an amino-substituted carbonyl and includes a moiety that can be represented by the general formula:

wherein $R_9$, $R_{10}$ are as defined above. Preferred embodiments of the amide will not include imides, which may be unstable.

The term "aralkyl", as used herein, refers to an alkyl group substituted with an aryl group (e.g., an aromatic or heteroaromatic group).

The term "aryl" as used herein includes 5-, 6-, and 7-membered single-ring aromatic groups that may include from zero to four heteroatoms, for example, benzene, pyrrole, furan, thiophene, imidazole, oxazole, thiazole, triazole, pyrazole, pyridine, pyrazine, pyridazine and pyrimidine, and the like. Those aryl groups having heteroatoms in the ring structure may also be referred to as "aryl heterocycles" or "heteroaromatics." The aromatic ring can be substituted at one or more ring positions with such substituents as described above, for example, halogen, azide, alkyl, aralkyl, alkenyl, alkynyl, cycloalkyl, hydroxyl, alkoxyl, amino, nitro, sulfhydryl, imino, amido, phosphate, phosphonate, phosphinate, carbonyl, carboxyl, silyl, ether, alkylthio, sulfonyl, sulfonamido, ketone, aldehyde, ester, heterocyclyl, aromatic or heteroaromatic moieties, —CF$_3$, —CN, or the like. The term "aryl" also includes polycyclic ring systems having two or more cyclic rings in which two or more carbons are common to two adjoining rings (the rings are "fused rings") wherein at least one of the rings is aromatic, e.g., the other cyclic rings can be cycloalkyls, cycloalkenyls, cycloalkynyls, aryls and/or heterocyclyls.

The term "carbocycle", as used herein, refers to an aromatic or non-aromatic ring in which each atom of the ring is carbon.

The term "carbonyl" is art-recognized and includes such moieties as can be represented by the general formula:

wherein X is a bond or represents an oxygen or a sulfur, and $R_{11}$ represents a hydrogen, an alkyl, an alkenyl, —(CH$_2$)$_m$—R$_8$ or a pharmaceutically acceptable salt, $R'_{11}$ represents a hydrogen, an alkyl, an alkenyl or —(CH$_2$)$_m$—R$_8$, where m and $R_8$ are as defined above. Where X is an oxygen and $R_{11}$ or $R'_{11}$ is not hydrogen, the formula represents an "ester". Where X is an oxygen, and $R_{11}$ is as defined above, the moiety is referred to herein as a carboxyl group, and particularly when $R_{11}$ is a hydrogen, the formula represents a "carboxylic acid". Where X is an oxygen, and $R'_{11}$ is hydrogen, the formula represents a "formate". In general, where the oxygen atom of the above formula is replaced by sulfur, the formula represents a "thiocarbonyl" group. Where X is a sulfur and $R_{11}$ or $R'_{11}$ is not hydrogen, the formula represents a "thioester." Where X is a sulfur and $R_{11}$ is hydrogen, the formula represents a "thiocarboxylic acid." Where X is a sulfur and $R_{11}'$ is hydrogen, the formula represents a "thiolformate." On the other hand, where X is a bond, and $R_{11}$ is not hydrogen, the above formula represents a "ketone" group. Where X is a bond, and $R_{11}$ is hydrogen, the above formula represents an "aldehyde" group.

The term "heteroatom" as used herein means an atom of any element other than carbon or hydrogen. Preferred heteroatoms are boron, nitrogen, oxygen, phosphorus, sulfur and selenium.

The terms "heterocyclyl" or "heterocyclic group" refer to 3- to 10-membered ring structures, more preferably 3- to 7-membered rings, whose ring structures include one to four heteroatoms. Heterocycles can also be polycycles. Heterocyclyl groups include, for example, thiophene, thianthrene, furan, pyran, isobenzofuran, chromene, xanthene, phenoxathiin, pyrrole, imidazole, pyrazole, isothiazole, isoxazole, pyridine, pyrazine, pyrimidine, pyridazine, indolizine, isoindole, indole, indazole, purine, quinolizine, isoquinoline, quinoline, phthalazine, naphthyridine, quinoxaline, quinazoline, cinnoline, pteridine, carbazole, carboline, phenanthridine, acridine, pyrimidine, phenanthroline, phenazine, phenarsazine, phenothiazine, furazan, phenoxazine, pyrrolidine, oxolane, thiolane, oxazole, piperidine, piperazine, morpholine, lactones, lactams such as azetidinones and pyrrolidinones, sultams, sultones, and the like. The heterocyclic ring can be substituted at one or more positions with such substituents as described above, as for example, halogen, alkyl, aralkyl, alkenyl, alkynyl, cycloalkyl, hydroxyl, amino, nitro, sulfhydryl, imino, amido, phosphate, phosphonate, phosphinate, carbonyl, carboxyl, silyl, ether, alkylthio, sulfonyl, ketone, aldehyde, ester, a heterocyclyl, an aromatic or heteroaromatic moiety, —$CF_3$, —CN, or the like.

As used herein, the term "nitro" means —$NO_2$; the term "halogen" designates —F, —Cl, —Br or —I; the term "sulfhydryl" means —SH; the term "hydroxyl" means —OH; and the term "sulfonyl" means —$SO_2$—.

The terms "polycyclyl" or "polycyclic group" refer to two or more rings (e.g., cycloalkyls, cycloalkenyls, cycloalkynyls, aryls and/or heterocyclyls) in which two or more carbons are common to two adjoining rings, e.g., the rings are "fused rings". Rings that are joined through non-adjacent atoms are termed "bridged" rings. Each of the rings of the polycycle can be substituted with such substituents as described above, as for example, halogen, alkyl, aralkyl, alkenyl, alkynyl, cycloalkyl, hydroxyl, amino, nitro, sulfhydryl, imino, amido, phosphate, phosphonate, phosphinate, carbonyl, carboxyl, silyl, ether, alkylthio, sulfonyl, ketone, aldehyde, ester, a heterocyclyl, an aromatic or heteroaromatic moiety, —$CF_3$, —CN, or the like.

A "selenoalkyl" refers to an alkyl group having a substituted seleno group attached thereto. Exemplary "selenoethers" which may be substituted on the alkyl are selected from one of —Se-alkyl, —Se-alkenyl, —Se-alkynyl, and —Se—$(CH_2)_m$—$R_8$, m and $R_8$ being defined above.

As used herein, the term "substituted" is contemplated to include all permissible substituents of organic compounds. In a broad aspect, the permissible substituents include acyclic and cyclic, branched and unbranched, carbocyclic and heterocyclic, aromatic and nonaromatic substituents of organic compounds. Illustrative substituents include, for example, those described herein above. The permissible substituents can be one or more and the same or different for appropriate organic compounds. For purposes of this invention, the heteroatoms such as nitrogen may have hydrogen substituents and/or any permissible substituents of organic compounds described herein which satisfy the valences of the heteroatoms. This invention is not intended to be limited in any manner by the permissible substituents of organic compounds.

It will be understood that "substitution" or "substituted with" includes the implicit proviso that such substitution is in accordance with permitted valence of the substituted atom and the substituent, and that the substitution results in a stable compound, e.g., which does not spontaneously undergo transformation such as by rearrangement, cyclization, elimination, etc.

Analogous substitutions can be made to alkenyl and alkynyl groups to produce, for example, aminoalkenyls, aminoalkynyls, amidoalkenyls, amidoalkynyls, iminoalkenyls, iminoalkynyls, thioalkenyls, thioalkynyls, carbonyl-substituted alkenyls or alkynyls.

As used herein, the definition of each expression, e.g., alkyl, m, n, etc., when it occurs more than once in any structure, is intended to be independent of its definition elsewhere in the same structure.

The terms triflyl, tosyl, mesyl, and nonaflyl are art-recognized and refer to trifluoromethanesulfonyl, p-toluenesulfonyl, methanesulfonyl, and nonafluorobutanesulfonyl groups, respectively. The terms triflate, tosylate, mesylate, and nonaflate are art-recognized and refer to trifluoromethanesulfonate ester, p-toluenesulfonate ester, methanesulfonate ester, and nonafluorobutanesulfonate ester functional groups and molecules that contain said groups, respectively.

The abbreviations Me, Et, Ph, Tf, Nf, Ts, Ms represent methyl, ethyl, phenyl, trifluoromethanesulfonyl, nonafluorobutanesulfonyl, p-toluenesulfonyl and methanesulfonyl, respectively. A more comprehensive list of the abbreviations utilized by organic chemists of ordinary skill in the art appears in the first issue of each volume of the Journal of Organic Chemistry; this list is typically presented in a table entitled Standard List of Abbreviations. The abbreviations contained in said list, and all abbreviations utilized by organic chemists of ordinary skill in the art are hereby incorporated by reference.

Certain compounds of the present invention may exist in particular geometric or stereoisomeric forms. The present invention contemplates all such compounds, including cis- and trans-isomers, R- and S-enantiomers, diastereomers, (D)-isomers, (L)-isomers, the racemic mixtures thereof, and other mixtures thereof, as falling within the scope of the invention. Additional asymmetric carbon atoms may be present in a substituent such as an alkyl group. All such isomers, as well as mixtures thereof, are intended to be included in this invention.

If, for instance, a particular enantiomer of a compound of the present invention is desired, it may be prepared by asymmetric synthesis, or by derivation with a chiral auxiliary, where the resulting diastereomeric mixture is separated and the auxiliary group cleaved to provide the pure desired enantiomers. Alternatively, where the molecule contains a basic functional group, such as amino, or an acidic functional group, such as carboxyl, diastereomeric salts may be formed with an appropriate optically active acid or base, followed by resolution of the diastereomers thus formed by fractional crystallization or chromatographic means well known in the art, and subsequent recovery of the pure enantiomers.

The chemical elements are identified herein in accordance with the Periodic Table of the Elements, CAS version, Handbook of Chemistry and Physics, 67th Ed., 1986-87, inside cover. Also for purposes of this invention, the term "hydrocarbon" is contemplated to include all permissible compounds having at least one hydrogen and one carbon atom. In a broad aspect, the permissible hydrocarbons include acyclic and cyclic, branched and unbranched, carbocyclic and heterocyclic, aromatic and nonaromatic organic compounds which can be substituted or unsubstituted.

The refractive indices of the silicon or germanium containing compounds, used as at least one component of an immersion fluid, can result in immersion fluids having high refractive indices (e.g., greater than about 1.35, or about 1.4, or about 1.5) at short wavelengths, e.g., at about 157 nm. This represents a significant leap above the current 157-nm immersion fluid technology. A 157-nm immersion fluid with such high refractive indices would allow for optical lithography up to the 22-nm node and potentially push back necessity for EUV technology for another decade. As well, such fluids can also have reasonably high indices of refraction at 193-nm (e.g., about 1.4) or other wavelengths. Accordingly, in some cases, an immersion fluid of the invention can be used at two or more lithographic wavelengths (e.g., 157-nm and/or 193-nm and/or 248-nm), which gives the immersion fluid flexibility in terms of range of use and economy.

Immersion fluids, consistent with embodiments of the invention, can find a variety of applications, e.g., in the area of microlithography and more specifically in the area of chemicals employed in lithography. The potential cost advantages of this technology along with the improved lithographic performance can render it the technology of choice for advanced 193-nm and 157-nm lithography in integrated circuit fabrication. Such immersion fluids, and the associated processes for their use, can be especially useful for the upcoming generation of 157-nm immersion lithography, where they can provide an alternative to EUV technology for 32-nm and lower wavelength imaging.

EXAMPLES

The following examples are provided to illustrate some embodiments of the invention. In particular, some of the examples provide what is believed to be the first examples of the use of a germanium-containing compound and a silicon-containing compound in an immersion fluid. The examples are not intended to limit the scope of any particular embodiment(s) utilized, as some of the immersion fluids can also be used at other wavelengths.

Example 1

Synthesis of Tris(dimethylamino)methylsilane (Material 1)

2M Dimethylamine in THF (200 ml, 6 eq) was added drop wise under nitrogen to trichloromethyl silane (7.87 ml, 67.0 mmol) cooled to 0° C. in an ice bath. A precipitate rapidly forms and the reaction exotherms. The reaction was let stir for 30 min after completion of addition, and solid filtered. THF was removed in vacuo and the light orange liquid was used without further purification.

Example 2

Synthesis of Tri(1H,1H-perfluorooctyl-1-oxy)methylsilane (Material 2)

Tris(dimethylamino)methylsilane 1 (3.76 g, 21.3 mmol) was added directly to 1H,1H-pentafluorooctan-1-ol (25.60 g, 64.0 mmol, 3 eq) in a round bottom flask fitted with a condenser. The reaction was stirred and refluxed overnight at 150° C. Progress of the reaction was monitored by FTIR from the disappearance of the hydroxyl group on the alcohol (3200-3500 $cm^{-1}$). The crude product was purified by vacuum distillation and afforded a colorless liquid in 84% yield; b.p. 180° C./2.3 Torr.

Example 3

Synthesis of Tri(1,1H-perfluoro-3,6,9-trioxdecyl-1-oxy)methylsilane (Material 3)

1H,1H-perfluoro-3,6,9-trioxdecan-1-ol (70.0 g, 176.0 mmol, 3 eq) was added directly to Tris(dimethylamino)methylsilane 1 (10.27 g, 58.6 mmol) in a round bottom flask fitted with a condenser. The reaction was stirred and refluxed overnight at 150° C. Progress of the reaction was monitored by FTIR from the disappearance of the hydroxyl group on the alcohol (3200-3500 $cm^{-1}$). The crude product was purified by vacuum distillation and afforded a colorless liquid in 89% yield; b.p. 152° C./4.4 Torr.

Example 4

Synthesis of Tri(1H,1H-heptafluoro-1-butoxy)methylsilane (Material 4)

1H,1H-heptafluoro-1-butanol (68.5 g, 342.0 mmol, 3 eq) was added drop wise by addition funnel to tris(dimethylamino)methylsilane 1 (20 g, 114.0 mmol) in a round bottom flask fitted with a condenser. The reaction exothermed and refluxed upon addition of the fluoro alcohol. The reaction was stirred at 80° C. for 6 hrs and refluxed overnight at 130° C. Progress of the reaction was monitored by FTIR from the disappearance of the hydroxyl group on the alcohol (3200-3500 $cm^{-1}$). The crude product was purified by vacuum distillation and afforded a colorless liquid in 63% yield; b.p. 79° C./1.4 Torr.

Example 5

Synthesis of Tetra(1H,1H-perfluorooctyl-1-oxy)silane (Material 5)

Tetrakis(dimethylamino)silane (6.39 g, 31.2 mmol) was added directly to 1H,1H-pentafluorooctan-1-ol (50.0 g, 125.0 mmol, 4 eq) in a round bottom flask fitted with a condenser. The reaction was stirred and refluxed overnight at 90° C., and an additional 8 hrs at 140° C. Progress of the reaction was monitored by FTIR from the disappearance of the hydroxyl group on the alcohol (3200-3500 $cm^{-1}$). The crude product was purified by vacuum distillation and afforded a light orange gelled liquid in 84% yield; b.p. 202° C./2.2 Torr.

Example 6

Synthesis of Tetra(1H,1H-heptafluoro-1-butoxy)silane (Material 6)

Tetrakis(dimethylamino)silane (12.8 g, 62.5 mmol) was added directly to 1H,1H-heptafluoro-1-butanol (50.0 g, 250.0 mmol, 4 eq) in a round bottom flask fitted with a condenser. The reaction was stirred and refluxed overnight at 135° C. Progress of the reaction was monitored by FTIR from the disappearance of the hydroxyl group on the alcohol (3200-3500 $cm^{-1}$). The crude product was purified by vacuum distillation and afforded a colorless liquid in 84% yield; b.p. 105° C./1.5 Torr.

Example 7

Synthesis of Tris(dimethylamino)tridecafluoro-1,1,2,2-tetrahydrooctylsilane (Material 7)

2M Dimethylamine in THF (161 ml, 6 eq) was added drop wise under nitrogen to tridecafluoro-1,1,2,2-tetrahydrooctyl trichlorosilane (26 g, 53.9 mmol) cooled to 0° C. in an ice bath. A precipitate rapidly forms and the reaction exotherms. The reaction was let stir for 30 min after completion of addition, and solid filtered. THF was removed in vacuo and the light orange liquid (83.6%) was used without further purification.

Example 8

Synthesis of Tri(1H,1H-perfluorooctyl-1-oxy)tridecafluoro-1,1,2,2-tetrahydrooctylsilane silane (Material 8)

Tris(dimethylamino)tridecafluoro-1,1,2,2-tetrahydrooctylsilane 8 (15 g, 29.6 mmol) was added directly to 1H,1H-pentafluorooctan-1-ol (35.50 g, 88.8 mmol, 3 eq) in a round bottom flask fitted with a condenser. The reaction was stirred and refluxed overnight at 150° C. Progress of the reaction was monitored by FTIR from the disappearance of the hydroxyl group on the alcohol (3200-3500 cm$^{-1}$). The crude product was purified by vacuum distillation and afforded a colorless liquid in 42% yield; b.p. 202° C./1.52 Torr.

Example 9

Synthesis of Tetramethyl tetra(1H,1H-perfluorooctyl-1-oxy)tetracyclosiloxane (Material 9)

To a stirred solution of 1,3,5,7-tetramethylcyclosiloxane (5.0 g, 20.8 mmol) in anhydrous toluene (350 ml), 1H,1H-pentafluorooctan-1-ol (39.9 g, 100.0 mmol, 4.8 eq) was added. Tris(pentafluorophenyl)borane (21.3 mg, 0.05% [B]/[Si—H]) was dissolved separately in 10 ml anhydrous toluene and added drop wise over 3 hrs. Hydrogen evolves rapidly upon addition of the borane catalyst. The disappearance of the Si—H stretch (2100 cm$^{-1}$) was monitored by FTIR. The reaction was stirred overnight at 100° C. The solvent was removed in vacuo and the remaining liquid was filtered and purified by vacuum distillation. 54% yield; b.p. 177° C./466 mTorr.

Example 10

Synthesis of Tetramethyl tetra(1H,1H-heptafluoro-1-butoxy)tetracyclosiloxane (Material 10)

To a stirred solution of 1,3,5,7-tetramethylcyclosiloxane (3.0 g, 12.5 mmol) in anhydrous toluene (200 ml), 1H,1H-heptafluoro-1-butanol (12.0 g, 59.9 mmol, 4.8 eq) was added. Tris(pentafluorophenyl)borane (12.8 mg, 0.05% [B]/[Si—H]) was dissolved separately in 4 ml anhydrous toluene and added drop wise over 3 hrs. Hydrogen evolves rapidly upon addition of the borane catalyst. The disappearance of the Si—H stretch (2100 cm$^{-1}$) was monitored by FTIR. The reaction was stirred overnight at room temperature. The solvent was removed in vacuo and the remaining liquid was filtered and purified by vacuum distillation. 41.6% yield; b.p. 135° C./2.35 Torr.

Example 11

Synthesis of Tetramethyl tetra(2,2,2-trifluoroethoxy)tetracyclosiloxane (Material 11)

2,2,2-trifluoroethanol (12.9 ml, 180.0 mmol, 4.8 eq) was added to a stirred solution of 1,3,5,7-tetramethylcyclosiloxane (9.0 g, 37.4 mmol) in anhydrous toluene (60 ml). Tris(pentafluorophenyl)borane (38.4 mg, 0.05% [B]/[Si—H]) was dissolved separately in 10 ml anhydrous toluene and added drop wise over 3 hrs. Hydrogen evolves rapidly upon addition of the borane catalyst. The disappearance of the Si—H stretch (2100 cm$^{-1}$) was monitored by FTIR. The reaction was stirred overnight at room temperature. The solvent was removed in vacuo and the remaining liquid was filtered and purified by vacuum distillation. 41.6% yield; b.p. 93° C./540 mTorr.

Example 12

Synthesis of Tris(dimethylamino)methylgermane (Material 12)

In an inert atmosphere, lithium dimethylamide (5.4 g, 106 mmol, 3.25 eq) was added to 100 ml anhydrous ether in a round bottom flask and cooled to −50° C. in a dry ice/acetone bath. Tricholoromethylgermane (6.35 g, 32.7 mmol) was added drop wise in a nitrogen purged syringe and a white precipitate rapidly forms. The reaction is warmed to room temperature over 3 hrs and stirred at room temperature and additional 2 hrs. Removal of solvent in vacuo leaves a cloudy liquid, which is unstable in air. The crude product had a 29% yield and was used without any further purification.

Example 13

Synthesis of Tri(1H,1H-heptafluoro-1-butoxy)methylgermane (Material 13)

1H,1H-heptafluoro-1-butanol (19.6 g, 98.11 mmol, 3 eq) was added drop wise by addition funnel to tris(dimethylamino)methylgermane 13 (7.2 g, 32.7 mmol) in a round bottom flask fitted with a condenser. The reaction exothermed and refluxed upon addition of the fluoro alcohol. The reaction was slowly heated to 135° C. and refluxed overnight. Progress of the reaction was monitored by FTIR from the disappearance of the hydroxyl group on the alcohol (3200-3500 cm$^{-1}$). The dark orange crude product was purified by vacuum distillation and afforded a colorless liquid in 41% yield; b.p. 75° C./151 mTorr.

Example 14

Synthesis of Tri(1H,1H,2H,2H-nonafluoro-1-hexyloxy)methylgermane (Material 14)

1H,1H,2H,2H-nonafluoro-1-hexanol (7.22 g, 27.4 mmol, 3 eq) was added drop wise by addition funnel to tris(dimethylamino)methylgermane 3 (2.0 g, 9.1 mmol) in a round bottom flask fitted with a condenser. The reaction exothermed and refluxed upon addition of the fluoro alcohol. The reaction was slowly heated to 135° C. and refluxed 48 hrs. Progress of the reaction was monitored by FTIR from the disappearance of the hydroxyl group on the alcohol (3200-3500 cm$^{-1}$). The dark orange crude product was purified by vacuum distillation and afforded a colorless liquid; b.p. 30° C./1.0 Torr.

Example 15

Synthesis of Octamethylcyclogermanoxane (Material 15)

Dimethyl dichlorogermane (21.8 g, 125 mmol) was added dropwise to a mixture of aqueous NaOH (9.85 g in 10 ml water) and 30 ml petroleum ether in a round bottom flask fitted with a condenser. This mixture was refluxed for 4 hrs and white solid precipitated. The organic layer was separated. The aqueous phase was extracted 4× with ether. All organic fractions were combined and dried with MgSO$_4$. Solvents were removed in vacuo and the product was dried on a vacuum rack to yield a clear liquid in 45% yield.

Example 16

Synthesis of Octaethylcyclogermanoxane (Material 16)

Diethyl dichlorogermane (25.3 g, 125 mmol) was added dropwise to a mixture of aqueous NaOH (9.85 g in 10 ml water) and 30 ml petroleum ether in a round bottom flask fitted with a condenser. A white solid precipitated and the mixture was refluxed for 4 hrs. The organic layer was separated. The aqueous phase was extracted 4× with ether. All organic fractions were combined and dried with $MgSO_4$. Solvents were removed in vacuo and the product was dried on a vacuum rack affording a clear liquid in 32% yield.

Example 17

Octamethylcyclotetrasiloxane (Material 17)

Octamethylcyclotetrasiloxane was purchased from Gelest Inc. and purified by vacuum distillation.

Example 18

Octamethyltrisiloxane (Material 18)

Octamethyltrisiloxane was purchased from Gelest Inc. and purified by vacuum distillation.

Example 19

Tetraethoxysilane (Material 19)

Tetraethoxysilane was purchased from Aldrich and purified by vacuum distillation.

Example 20

Tetraethoxygermanium (Material 20)

Tetraethoxygermanium was purchased from Gelest Inc. and purified by vacuum distillation.

Example 21

Tetramethoxygermanium (Material 21)

Tetramethoxygermanium was purchased from Gelest Inc. and purified by vacuum distillation.

Example 22

Tri(1H,1H,2H,2H-nonafluoro-1-hexyloxy)methylsilane (Material 22)

1H,1H,2H,2H-nonafluoro-1-hexanol (22.58 g, 171.0 mmol, 3 eq) was added drop wise by addition funnel to tris(dimethylamino)methylsilane 3 (5.0 g, 57.0 mmol) in a round bottom flask fitted with a condenser. The mixture was slowly heated to 140° C. and refluxed overnight. Progress of the reaction was monitored by FTIR from the disappearance of the hydroxyl group on the alcohol (3200-3500 $cm^{-1}$). The orange crude product was purified by vacuum distillation and afforded a colorless liquid; b.p. 125° C./0.67 Torr.

Example 23

Tri Tetramethyl tetra(1H,1H,2H,2H-nonafluoro-1-hexyloxy)tetracyclosiloxane (Material 23)

To a stirred solution of 1,3,5,7-tetramethylcyclosiloxane (5 g, 20.8 mmol) in anhydrous toluene (232 ml), 1H,1H,2H,2H-nonafluoro-1-hexanol (16.6 g, 99.8 mmol, 4.8 eq) was added. Tris(pentafluorophenyl)borane (21.3 mg, 0.05% [B]/[Si—H]) was dissolved separately in 10 ml anhydrous toluene and added drop wise over 3 hrs. The disappearance of the Si—H stretch (2100 $cm^{-1}$) was monitored by FTIR. The reaction was heated to 90° C. and stirred overnight. The solvent was removed in vacuo and the remaining liquid was filtered and purified by vacuum distillation. 49.3% yield; b.p. 148° C./4.82 Torr.

Example 24

Tetramethyl tetra(1H-1H-nonafluoro-3,6-dioxaheptoxy)tetracyclosiloxane (Material 24)

To a stirred solution of 1,3,5,7-tetramethylcyclosiloxane (5 g, 20.8 mmol) in anhydrous toluene (350 ml), 1H-1H-nonafluoro-3,6-dioxaheptanol (21.8 g, 100.0 mmol, 4.8 eq) was added. Tris(pentafluorophenyl)borane (21.3 mg, 0.05% [B]/[Si—H]) was dissolved separately in 10 ml anhydrous toluene and added drop wise over 3 hrs. The disappearance of the Si—H stretch (2100 $cm^{-1}$) was monitored by FTIR. The reaction was stirred for 48 hrs at room temperature. The solvent was removed in vacuo and the remaining liquid was filtered and purified by vacuum distillation. 56.9% yield; b.p. 145° C./0.930 Torr.

Example 25

Tetramethyl tetraethoxy tetracyclosiloxane (Material 25)

To a stirred solution of 1,3,5,7-tetramethylcyclosiloxane (10 g, 41.5 mmol) in anhydrous toluene (500 ml), ethanol (11.64 ml, 200.0 mmol, 4.8 eq) was added. Tris(pentafluorophenyl)borane (42.6 mg, 0.05% [B]/[Si—H]) was dissolved separately in 10 ml anhydrous toluene and added drop wise over 3 hrs. The disappearance of the Si—H stretch (2100 $cm^{-1}$) was monitored by FTIR. The reaction was stirred for 24 hrs at 90° C. The solvent was removed in vacuo and the remaining liquid was filtered and purified by vacuum distillation. 51.2% yield; b.p. 98° C./0.835 Torr.

Example 26

Tetramethyl tetramethoxy tetracyclosiloxane (Material 26)

To a stirred solution of 1,3,5,7-tetramethylcyclosiloxane (10 g, 41.5 mmol) in anhydrous toluene (200 ml), methanol (6.40 g, 200.0 mmol, 4.8 eq) was added. Tris(pentafluorophenyl)borane (42.6 mg, 0.05% [B]/[Si—H]) was dissolved separately in 10 ml anhydrous toluene and added drop wise over 3 hrs. The disappearance of the Si—H stretch (2100 $cm^{-1}$) was monitored by FTIR. The reaction was stirred for 24 hrs at 90° C. The solvent was removed in vacuo and the remaining liquid was filtered and purified by vacuum distillation. 97.8% yield; b.p. 102° C./4.38 Torr.

Material Structures

-continued

Material 14

Material 15

Material 16

Material 17

Material 18

Material 19

Material 20

Material 21

Material 22

Material 23

-continued

Material 24

Material 25

Material 26

Example 27

Determining Refractive Indices at 157.6 nm

Refractive Indicies were determined at 157.6 nm using the Woolam Company VUV-VASE spectroscopic ellipsometer system, WVASE32. The fluids were deposited onto roughened glass microscope Slides and scanned through Brewster's angle in the VUV-VASE with reflection mode ellipsometry. Ellipsometric psi and delta data were acquired. Measurements over a wide range of incident angles at fixed wavelengths of 157.6 nm, 193.4 nm, and 248.0 nm were recorded. The measured psi data was modeled with the Cauchy dispersion model. The index of refraction, n(λ), is given by, $$n(\lambda) = A_n + \frac{B_n}{\lambda^2} + \frac{C_n}{\lambda^4},$$

where $A_n$, $B_n$, and $C_n$, are Cauchy Parameters and λ is the wavelength in microns. The refractive indices at 157.6 nm, 193.4 nm, and 248.0 nm for different silicon containing fluids is given in Table 1 with an accuracy of ±0.001

TABLE 1

| Refractive indices (RI) at 157.6 nm | |
|---|---|
| Material | RI at 157.6 nm |
| 2 | 1.440 |
| 3 | 1.377 |

TABLE 1-continued

| Refractive indices (RI) at 157.6 nm | |
|---|---|
| Material | RI at 157.6 nm |
| 4 | 1.424 |
| 8 | 1.455 |
| 9 | 1.494 |
| 10 | 1.494 |

The results show that the silicon containing material all have an index of refraction at 157.6 nm significantly larger than 1.00 and most have an index of refraction at 157.6 nm of greater than 1.400. All of these fluids are expected to allow for increased resolution and depth of focus when employed in 157-nm immersion lithography.

Example 28

Determining Refractive Index at 157.6 nm, 193.4 nm and 248.0 nm

Refractive Indices were determined at 157.6, 193.4, and 248.0 nm using the Woolam Company VUV-VASE spectroscopic ellipsometer system, WVASE32. The fluids were placed in a hollow prism cell and the refractive index determined using the prism minimum deviation technique. The minimum deviation was measured at a range of wavelengths from 147 to 308 nm and the refractive index at 157.6, 193.4, and 248.0 nm was determined. The refractive index at 157.6 193.4, and 248.0 nm for different silicon containing fluids is given in Table 2 with an accuracy of ±0.001.

TABLE 2

Refractive indicies at 157.6 nm, 193.4 nm, and 248.0 nm

| Material | RI at 157.6 nm | RI at 193.4 nm | RI at 248.0 nm |
|---|---|---|---|
| 2 | 1.440 | 1.341 | 1.313 |
| 3 | 1.377 | 1.360 | 1.327 |

The results show that the silicon containing materials all have an index of refraction at 157.6 nm significantly larger than 1.00 and one has an index of refraction at 157.6 nm of greater than 1.400. All of these fluids are expected to allow for increased resolution and depth of focus when employed in 157-nm immersion lithography. The results also show that silicon containing materials can also have an index of refraction at 193.4 and 248.0 nm significantly larger than 1.30. These fluids are expected to allow for increased resolution and depth of focus when employed in 193- or 248-nm immersion lithography.

Example 29

Determining Refractive Indices

A Cary 400 Varian VUV spectrophotometer was used to obtain 157.6 nm and 193.4 nm refractive index measurements. A roughened glass slide was wetted with the fluid and percent reflectance measured by reflection mode spectroscopy. The reflection is equivalent to that from the bulk of the liquid and is given by the equation for normal incidence irradiation:

$$R = \frac{(n-1)^2 + k^2}{(n+1)^2 + k^2},$$

where n and k are real and imaginary parts of refractive index. This equation is then solved for n in terms of R. k is estimated from separate absorbance measurements. The refractive indicies at 157.6 nm and 193.4 nm for different silicon and germanium containing fluids are given in Table 3 with an accuracy of ±0.005. Entries with "na" were not available.

TABLE 3

Refractive indices (RI) at 157.6 nm and 193.4 nm

| Material | RI at 157.6 nm | RI at 193.4 nm |
|---|---|---|
| 4 | 1.410 | 1.353 |
| 8 | na | 1.368 |
| 9 | na | 1.391 |
| 10 | 1.485 | 1.395 |
| 11 | 1.530 | 1.428 |
| 13 | 1.440 | 1.384 |
| 14 | 1.400 | 1.369 |
| 15 | 1.635 | 1.720 |
| 16 | 1.770 | na |
| 17 | 1.505 | 1.537 |
| 20 | 1.555 | na |
| 22 | 1.440 | 1.380 |
| 23 | 1.530 | 1.407 |
| 24 | 1.440 | 1.378 |
| 25 | 1.665 | 1.484 |
| 26 | 1.620 | na |

The results show that the silicon and germanium containing materials all have an index of refraction at 157.6 nm significantly larger than 1.0 and all have an index of refraction at 157.6 nm of greater than 1.4. Several of the fluids have an index of refraction at 157.6 nm of greater than 1.5 and two of the germanium containing materials have an index of refraction 157.6 nm of greater than 1.6. All of these fluids are expected to allow for increased resolution and depth of focus when employed in 157-nm immersion lithography.

The results also show that silicon germanium containing materials all have an index of refraction at 193.4 nm significantly larger than 1.00 and all have an index of refraction at 157.6 nm of greater than 1.3. Several of the fluids have an index of refraction at 193.4 nm greater than 1.5. All of these fluids are expected to allow for increased resolution and depth of focus when employed in 193-nm immersion lithography.

Example 30

Determining Refractive Index at 589.6 nm

Refractive indices of liquid samples at 589.6 nm (sodium D line) were obtained on a Carl Zeiss Abbe Refractometer at 22° C. The refractive index at 589 nm for different silicon and germanium containing fluids is given in Table 4 with an accuracy of 0.001.

TABLE 4

Refractive index at 589 nm

| Material | RI at 589.6 nm |
|---|---|
| 2 | 1.3124 |
| 4 | 1.3055 |
| 6 | 1.3039 |
| 8 | 1.3154 |
| 9 | 1.3258 |
| 10 | 1.3320 |
| 11 | 1.3470 |
| 13 | 1.3231 |
| 14 | 1.3156 |
| 15 | 1.4733 |
| 16 | 1.4749 |
| 17 | 1.3968 |
| 18 | 1.3848 |
| 19 | 1.3818 |
| 20 | 1.4049 |
| 21 | 1.3688 |
| 22 | 1.3234 |
| 23 | 1.3449 |
| 24 | 1.3182 |
| 25 | 1.4005 |
| 26 | 1.4000 |

The results show that the silicon and germanium containing materials all have an index of refraction at 589.6 nm significantly larger than 1.00 and all have an index of refraction at 589.6 nm of greater than 1.300. Several of the fluids have an index of refraction at 589.6 nm of greater than 1.400. These results also show that the increase in index of refraction is not limited to 157.6 nm, 193.4 nm, and 248.0 nm, but also occurs at other wavelengths. All of these fluids are expected to allow for increased resolution and depth of focus when employed in 157-nm, 196-nm, or 248-nm immersion lithography.

Example 31

Absorbance Measurements at 157 and 193 nm with High Volatility Liquids

A Cary 400 Varian VUV spectrophotometer was used to measure the absorbance of some of the above exemplary immersion fluids at 193 nm. The immersion fluid was prepared with a freeze-pump-thaw method to dry and de-gas the samples before measurement. The fluid was frozen in liquid nitrogen, subjected to vacuum, and warmed to room temperature in a sealed tube. This sequence was repeated four times or until no gas evolved during the thawing step. The liquid was then placed in a liquid flow cell employing calcium fluoride windows fitted with 25 μm spacers to define the path length. The transmission was measured from 145 to 200 nm and the absorbance at 193 nm were calculated. The result is shown in Table 5.

TABLE 5

Absorbance Measurements at 193 nm

| Material | Absorbance at 193 nm ($\mu m^{-1}$) |
|---|---|
| 2 | 0.0006 |
| 4 | 0.0014 |
| 10 | 0.0017 |

The results show that the silicon containing materials have a 193 nm absorbance much lower than about 0.002 $\mu m^{-1}$. The will allow for an optical path length of much greater than about 500 micrometers at 193 nm. The fluid is expected to allow for increased resolution and depth of focus when employed in 157-nm, 193-nm, or 248-nm immersion lithography.

Example 32

Absorbance Measurements at 157 and 193 nm with Low Volatility Liquids

A Cary 400 Varian VUV spectrophotometer was used to measure the absorbance of some of the above exemplary immersion fluids at 157 and 193 nm. Liquid film thicknesses of between 700 and 2000 nm were spin cast on VUV-grade calcium fluoride windows. The transmission was measured from 145 to 200 nm and the absorbance at 157 and 193 nm was calculated. Film thickness was determined with a Luzchem TFA (Thin Film Analysis) both immediately before and transmission measurements and no change in film thickness was deserved. Typically 3 and in all cases at least 2 different film thicknesses were measured and the average value is reported in Table 6.

TABLE 6

Absorbance Measurements at 157 nm and 193 nm

| Material | Absorbance at 157 nm | Absorbance at 193 nm |
|---|---|---|
| 9 | 0.460 | <0.001 |
| 10 | 0.352 | 0.005 |
| 11 | 0.448 | <0.001 |
| 13 | na | 0.083 |
| 22 | 0.290 | 0.002 |
| 23 | 1.080 | 0.020 |
| 24 | 0.224 | <0.001 |
| 25 | 1.235 | <0.001 |

The results show that 5 of the silicon containing materials have a 157 nm absorbance lower than the 0.5 $\mu m^{-1}$ and that 3 of the silicon containing materials have a 157 nm absorbance much lower than the 0.5 $\mu m^{-1}$. This will allow for an optical path length of greater than about 2 micrometers at 157 nm. The results also show that the silicon containing materials have a 193 nm absorbance much lower than about 0.1 $\mu m^{-1}$. The results also show that 6 of the silicon containing materials have a 193 nm absorbance lower than about 0.01 $\mu m^{-1}$ and that 4 of the silicon containing materials have a 193 nm absorbance much lower than about 0.001 $\mu m^{-1}$. The will allow for an optical path length of much greater than about 100 micrometers for 6 of the materials and much greater than about 1000 micrometers for 4 of the materials at 193 nm. The fluids are expected to allow for increased resolution and depth of focus when employed in 157-nm, 193-nm, or 248-nm immersion lithography.

Example 33

Immersion Lithography at 157 nm

A silicon wafer was coated to a 50-nm thick film of Microchem Corp. PMMA A 2 as the resist and baked in a convection oven at 180° C. for 25 minutes. The resist was exposed on a liquid immersion interference lithography system based on a Jamin interferometer with a fluorine doped fused silica prism having a refractive index of 1.675 and employing 2.0 micrometers of Material 10 as a coupling medium between the prism and resist. The resist was exposed with 157-nm light to a dose of 200 mJ/cm². After exposure the resist was developed in a 1:3 mixture of methyl isobutyl ketone and isopropyl alcohol for 30 seconds followed by blow-drying with air. The resist exhibited approximately 27-nm half-pitch imaging with a 54.3 nm period. The theoretical period should be 54.3 nm with the immersion liquid but only 91.0 nm in air without an immersion liquid. The results show that Material 10 can be employed as a 157-nm immersion liquid and improved resolution can be obtained by employing silicon and germanium based immersion fluids with 157-nm immersion lithography.

While the present invention has been described in terms of specific methods, structures, and devices it is understood that variations and modifications will occur to those skilled in the art upon consideration of the present invention. For example, the methods and compositions discussed herein can be utilized beyond lithography for electronic materials production. As well, the features illustrated or described in connection with one embodiment may be combined with the features of other embodiments. Such modifications and variations are intended to be included within the scope of the present invention. Those skilled in the art will appreciate, or be able to ascertain using no more than routine experimentation, further features and advantages of the invention based on the above-described embodiments. Accordingly, the invention is not to be limited by what has been particularly shown and described, except as indicated by the appended claims. All publications and references are herein expressly incorporated by reference in their entirety.

What is claimed is:

1. A process for performing photolithography, comprising emitting radiation having at least one wavelength below about 260 nm; and
disposing a liquid such that the radiation passes through at least a portion of the liquid before impinging on a surface, the liquid exhibiting an index of refraction greater than about 1 for the at least one wavelength,
wherein the liquid comprises a compound having at least one Si—O bond, the liquid being deoxygenated, the liquid exhibiting an index of refraction greater than about 1 for at least one wavelength in a range of about 140 nm to about 260 nm, the liquid also exhibiting an absorption less than about 2 $\mu m^{-1}$ for at least one wavelength in the range of about 140 nm to about 260 nm, and wherein the at least one Si—O bond forms a cyclic structure with one or more additional Si—O bonds present in the compound.

2. A process for performing photolithography, comprising
emitting radiation having at least one wavelength below about 260 nm; and
disposing a liquid such that the radiation passes through at least a portion of the liquid before impinging on a surface, the liquid exhibiting an index of refraction greater than about 1 for the at least one wavelength,
wherein the liquid comprises a compound having at least one Si—O bond, at least one oxygen atom of the compound being bound to a silicon atom and a fluorinated moiety, wherein
(a) the fluorinated moiety is a linear fluorinated moiety, or a branched fluorinated moiety with at least 4 carbon atoms when
(i) the silicon atom is bound to an aliphatic moiety, and
(ii) the compound has only one silicon atom; and
(b) the fluorinated moiety has at least 4 carbon atoms when
(i) the silicon atom is bound to four oxygen atoms, and
(ii) the compound has only one silicon atom,
the compound having an index of refraction greater than 1 for at least one wavelength of light in a range of about 140 nm to about 260 nm when the compound is substantially pure and in a liquid state.

3. The process of claim 2, wherein the index of refraction of the compound is greater than about 1.3 for the at least one wavelength of light in the range of about 140 nm to about 260 nm.

4. The process of claim 2, wherein the compound has an absorbance less than about 1 $\mu m^{-1}$ for light having at least one wavelength in a range from about 140 nm to about 260 nm.

5. The process of claim 2, wherein the fluorinated moiety comprises any of a fluorinated alkyl, a fluorinated alkoxy, a fluorinated alkenyl, a fluorinated aryl, a fluorinated heteroaryl, a fluorinated silanyl, a fluorinated siloxynyl, a fluorinated germanyl, a fluorinated germanoxanyl or a fluorinated heteroalkyl.

6. The process of claim 2, wherein the compound comprises an organosilane.

7. The process of claim 1, wherein the at least one Si—O bond forms a cyclic structure with one or more additional Si—O bonds present in the compound.

8. A process for performing photolithography, comprising
emitting radiation having at least one wavelength below about 260 nm; and
disposing a liquid such that the radiation passes through at least a portion of the liquid before impinging on a surface, the liquid exhibiting an index of refraction greater than about 1 for the at least one wavelength, wherein the liquid comprises a liquid compound having at least one Ge—O bond, the liquid being deoxygenated, the liquid exhibiting an index of refraction greater than about 1 for at least one wavelength in a range of about 140 nm to about 260 nm, the liquid also exhibiting an absorption less than about 2 $\mu m^{-1}$ for at least one wavelength in the range of about 140 nm to about 260 nm.

9. The process of claim 8, wherein the liquid has a molecular oxygen concentration lower than about 1000 ppm.

10. The process of claim 8, wherein the compound exhibits a decomposition of less than about 1 weight percent after about 1 hour of exposure to air.

11. The process of claim 8, wherein the liquid exhibits an index of refraction greater than about 1.4 for at least one wavelength in a range of about 140 nm to about 160 nm.

12. The process of claim 8, wherein the liquid exhibits an index of refraction greater than about 1.3 at least in the range of about 140 nm to about 260 nm.

13. The process of claim 8, wherein the liquid exhibits an absorption less than about 1 $\mu m^{-1}$ for at least one wavelength in a range of about 140 nm to about 260 nm.

14. The process of claim 8, wherein the liquid exhibits an absorption less than about 1 $\mu m^{-1}$ for at least one wavelength in a range of about 140 nm to about 200 nm.

15. The process of claim 8, wherein the liquid exhibits an absorption less than about 1 $\mu m^{-1}$ for at least one wavelength in a range of about 140 nm to about 160 nm.

16. A process for performing photolithography, comprising
emitting radiation having at least one wavelength below about 260 nm; and
disposing a liquid such that the radiation passes through at least a portion of the liquid before impinging on a surface, the liquid comprising a compound having at least one Ge—O bond, the liquid exhibiting an index of refraction greater than about 1 for the at least one wavelength,
wherein the liquid comprises at least one fluorinated moiety.

17. The process of claim 16, wherein the fluorinated moiety comprises any of a fluorinated alkyl, a fluorinated alkoxy, a fluorinated alkenyl, a fluorinated aryl, a fluorinated heteroaryl, a fluorinated germanyl, a fluorinated germanoxanyl or a fluorinated heteroalkyl.

18. The process of claim 8, wherein a germanium atom of the at least one Ge—O bond is attached to at least one additional oxygen.

19. A process for performing photolithography, comprising
emitting radiation having at least one wavelength below about 260 nm; and
disposing a liquid such that the radiation passes through at least a portion of the liquid before impinging on a surface, the liquid comprising a compound having at least one Ge—O bond, the liquid exhibiting an index of refraction greater than about 1 for the at least one wavelength,
wherein the at least one Ge—O bond forms a cyclic structure with one or more additional Ge—O bonds present in the compound.

20. A process for performing photolithography, comprising
emitting radiation having at least one wavelength below about 260 nm; and
disposing a liquid such that the radiation passes through at least a portion of the liquid before impinging on a surface, the liquid comprising a compound having at least one Ge—O bond, the liquid exhibiting an index of refraction greater than about 1 for the at least one wavelength,
wherein the at least one Ge—O bond forms a caged structure with one or more additional Ge—O bonds present in the compound.

21. A process for performing photolithography, comprising
emitting radiation having at least one wavelength below about 260 nm; and
disposing a liquid such that the radiation passes through at least a portion of the liquid before impinging on a surface, the liquid exhibiting an index of refraction greater than about 1 for the at least one wavelength, wherein the liquid comprises a compound having at least one Ge—O bond and at least one fluorinated moiety, the compound having an index of refraction greater than 1 for at least one wavelength of light in a range of about 140 nm to about 260 nm.

22. The process of claim 21, wherein the index of refraction of the compound is greater than about 1.3 for the at least one wavelength of light in the range of about 140 nm to about 260 nm.

23. The process of claim 21, wherein the compound has an absorbance less than about 1 $\mu m^{-1}$ for light having at least one wavelength in a range from about 140 nm to about 260 nm.

24. The process of claim 21, wherein the fluorinated moiety comprises any of a fluorinated alkyl, a fluorinated alkoxy, a fluorinated alkenyl, a fluorinated aryl, a fluorinated heteroaryl, a fluorinated germanyl, a fluorinated germanoxanyl or a fluorinated heteroalkyl.

25. The process of claim 21, wherein a germanium atom attached to the at least one Ge—O bond is also attached to at least one additional oxygen.

26. The process of claim 21, wherein the at least one Ge—O bond forms a cyclic structure with one or more additional Ge—O bonds present in the compound.

* * * * *